United States Patent
Miyake et al.

(10) Patent No.: US 9,452,092 B2
(45) Date of Patent: Sep. 27, 2016

(54) ABSORBENT ARTICLE

(75) Inventors: Hirofumi Miyake, Tokushima (JP); Miyuki Okawa, Tokushima (JP); Akiko Tatsukawa, Tokushima (JP)

(73) Assignee: LIVEDO CORPORATION, Ehime (JP)

(*) Notice: Subject to any disclaimer, the term of this patent is extended or adjusted under 35 U.S.C. 154(b) by 332 days.

(21) Appl. No.: 14/118,777

(22) PCT Filed: May 23, 2012

(86) PCT No.: PCT/JP2012/003359
§ 371 (c)(1),
(2), (4) Date: Nov. 19, 2013

(87) PCT Pub. No.: WO2012/169129
PCT Pub. Date: Dec. 13, 2012

(65) Prior Publication Data
US 2014/0128829 A1 May 8, 2014

(30) Foreign Application Priority Data

Jun. 6, 2011 (JP) .................................. 2011-126420

(51) Int. Cl.
| | |
|---|---|
| *A61F 13/15* | (2006.01) |
| *A61F 13/494* | (2006.01) |
| *A61F 13/49* | (2006.01) |

(52) U.S. Cl.
CPC ......... *A61F 13/4942* (2013.01); *A61F 13/494* (2013.01); *A61F 13/49413* (2013.01);
(Continued)

(58) Field of Classification Search
CPC ................. A61F 13/49014; A61F 13/49011; A61F 13/49017; A61F 13/49015; A61F 2013/4903

USPC ............ 604/385.28, 385.27, 385.25, 385.24
See application file for complete search history.

(56) References Cited

U.S. PATENT DOCUMENTS

| | | | |
|---|---|---|---|
| 6,786,895 B1 | 9/2004 | Schmitz | |
| 2001/0021837 A1* | 9/2001 | Mizutani | A61F 13/4753 604/385.28 |

(Continued)

FOREIGN PATENT DOCUMENTS

| | | |
|---|---|---|
| CN | 1502315 A | 6/2004 |
| CN | 1939242 A | 4/2007 |

(Continued)

OTHER PUBLICATIONS

Second Notification of Office Action for Chinese Patent App. No. 201280027938.1 (Mar. 9, 2015) with English translation thereof.
(Continued)

*Primary Examiner* — Jacqueline Stephens
(74) *Attorney, Agent, or Firm* — Cermak Nakajima & McGowan LLP; Tomoko Nakajima

(57) ABSTRACT

Each side wall part on a main body part includes a strip-like pouch part and an elastic member. The pouch part includes a first strip part extending in the longitudinal direction, and a second strip part disposed between the first strip part and the main body part and having both its edges along the longitudinal direction connecting to both edges of the first strip part. The elastic member is bonded to the first strip part linearly in the longitudinal direction. A standing part is formed in the pouch part by contraction of the elastic member. In each end part of the pouch part, a state where the pouch part overlaps with the main body part is maintained. Therefore, the height of the standing part changes gradually in a boundary part between the end part and the central part, which allows the standing part to fit against the wearer's skin.

4 Claims, 5 Drawing Sheets

(52) U.S. Cl.
CPC .... *A61F13/49473* (2013.01); *A61F 13/49011* (2013.01); *A61F 13/49014* (2013.01); *A61F 13/49017* (2013.01); *A61F 2013/49039* (2013.01)

(56) References Cited

U.S. PATENT DOCUMENTS

| | | |
|---|---|---|
| 2004/0102756 A1 | 5/2004 | Ichiura et al. |
| 2005/0055004 A1 | 3/2005 | Turi et al. |

FOREIGN PATENT DOCUMENTS

| | | |
|---|---|---|
| EP | 2027842 A1 | 2/2009 |
| EP | 2027842 B1 | 2/2009 |
| EP | 2298261 A2 | 3/2011 |
| JP | 2004-000481 A | 1/2004 |

OTHER PUBLICATIONS

Office Action from Chinese Patent App. No. 201280027938.1 (Jul. 23, 2014) with English language translation thereof.

International Search Report and Written Opinion for PCT Patent App. No. PCT/JP2012/003359 (Aug. 17, 2012).

\* cited by examiner

II-II

III-III

ABSORBENT ARTICLE

This application is a national phase entry under 35 U.S.C. §371 of PCT Patent Application No. PCT/JP2012/003359, filed on May 23, 2012, which claims priority under 35 U.S.C. §119 to Japanese Patent Application No. 2011-126420, filed Jun. 6, 2011 both of which are incorporated by reference.

TECHNICAL FIELD

The present invention relates to an absorbent article for receiving body waste from a wearer.

BACKGROUND ART

Conventionally, absorbent articles such as disposable diapers have been configured such that two side wall parts are provided, one on each side of a main body part, and portions of the side wall parts that serve as standing parts stand up toward the wearer by contraction of elastic yarn or the like provided on free edges of the side wall parts. When an absorbent article is worn, the pair of standing parts serves as standing gathers that come into contact with the vicinity of the top of the wearer's legs, and as a result, seepage of body waste from the absorbent article is prevented.

In the disposable diaper disclosed in Japanese Patent Application Laid-Open No. 2004-481 (Document 1), inner sheets connected consecutively to a back sheet are disposed on both right and left sides on the top sheet side. At the inner edges of the inner sheets, extendable elastic members are disposed and fixed in their extended state, forming a pair of right and left pleated gathers. Furthermore, approximately central parts of the pleated gathers in the longitudinal direction and approximately central inner parts of leg gathers in the longitudinal direction are bonded to each other. As a result, in the disposable diaper of Document 1, not only the pleated gathers but also the leg gathers take a three-dimensional form, and leakage of liquid from around the wearer's legs is effectively prevented.

Incidentally, in the absorbent article, each side wall part (standing part) stands up high from the main body part in a central part that faces the crotch area of a wearer, whereas the side wall part overlaps with the main body part in end parts that contact the skin of the wearer on the front and back sides. Meanwhile, in parts between the end parts and the central part, the side wall part generally has the same structure as in the central part, and thus when the absorbent article is worn, the standing part (standing gathers) in the boundary parts is pushed down toward the main body part, making it difficult for the upper edge (free edge) of the standing part to closely fit against the skin of the wearer, and resulting in the risk that leakage of the body waste or the like will occur.

SUMMARY OF INVENTION

The present invention is intended for an absorbent article for receiving body waste from a wearer, and it is an object of the present invention to allow each standing part to fit against the skin of a wearer in boundary parts between end parts and a central part.

The absorbent article according to the present invention includes a generally sheet-like main body part having an absorbent core disposed between a back sheet and a top sheet, and two side wall parts that extend in a longitudinal direction of the main body part, one on each side of the main body part. Each side wall part includes a strip-like pouch part that includes a first strip part and a second strip part, the first strip part extending in the longitudinal direction on the main body part and the second strip part being disposed between the first strip part and the main body part and having both edges along the longitudinal direction connecting to both edges of the first strip part, in a state in which the main body part is stretched, and an elastic member that is bonded to the first strip part away from the edges of the first strip part, the elastic member extending linearly in the longitudinal direction and lying in a central part of the strip-like pouch part in the longitudinal direction. A standing part that stands up from the main body part is formed in the strip-like pouch part by contraction of the elastic member. In both end parts of the strip-like pouch part in the longitudinal direction, a state in which the first strip part and the second strip part overlap with each other and a state in which the second strip part overlaps with the main body part are maintained.

According to the present invention, each standing part can fit against the skin of a wearer in the boundary parts between the end parts and the central part.

In a preferred embodiment of the present invention, in the central part of the strip-like pouch part, the elastic member is located in approximately a center of the strip-like pouch part in a width direction that is perpendicular to the longitudinal direction. This allows the standing part to stand up high in the central part.

In this case, in order to bring the standing part into close contact with a wearer in the boundary parts, it is preferable that the elastic member is disposed from a vicinity of one end part of the strip-like pouch part to a vicinity of the other end part in the longitudinal direction, and distances between the elastic member and the edges of the first strip part in the vicinity of the end parts are shorter than the distances in the central part.

More preferably, the elastic member is a group of two string-like elastic elements that are disposed from the vicinity of the one end part to the vicinity of the other end part, and the two string-like elastic elements are close to each other in the width direction in the central part and are spaced from each other in the width direction in the vicinity of the end parts.

In another preferred embodiment of the present invention, two side sheets are disposed, one on each side of the main body part. Each side wall part is a portion of one of the side sheets. In each side wall part that is in the state in which the main body part is stretched, the second strip part is separated into a strip-like inner part and a strip-like outer part in a width direction that is perpendicular to the longitudinal direction. Each of the side sheets includes a first sheet base part that extends outward in the width direction from an inner edge of the outer part, between the outer part and the main body part, and a second sheet base part that is continuous with the inner part and extends outward in the width direction, between the first sheet base part and the main body part. In the end parts, a surface of the second sheet base part that faces the main body part is bonded to the main body part, and in a vicinity of the central part, the second sheet base part is bonded to the main body part outwardly of the strip-like pouch part. This allows the standing part to stand up high in the central part.

These and other objects, features, aspects and advantages of the present invention will become more apparent from the

DESCRIPTION OF EMBODIMENTS

Figure 1:
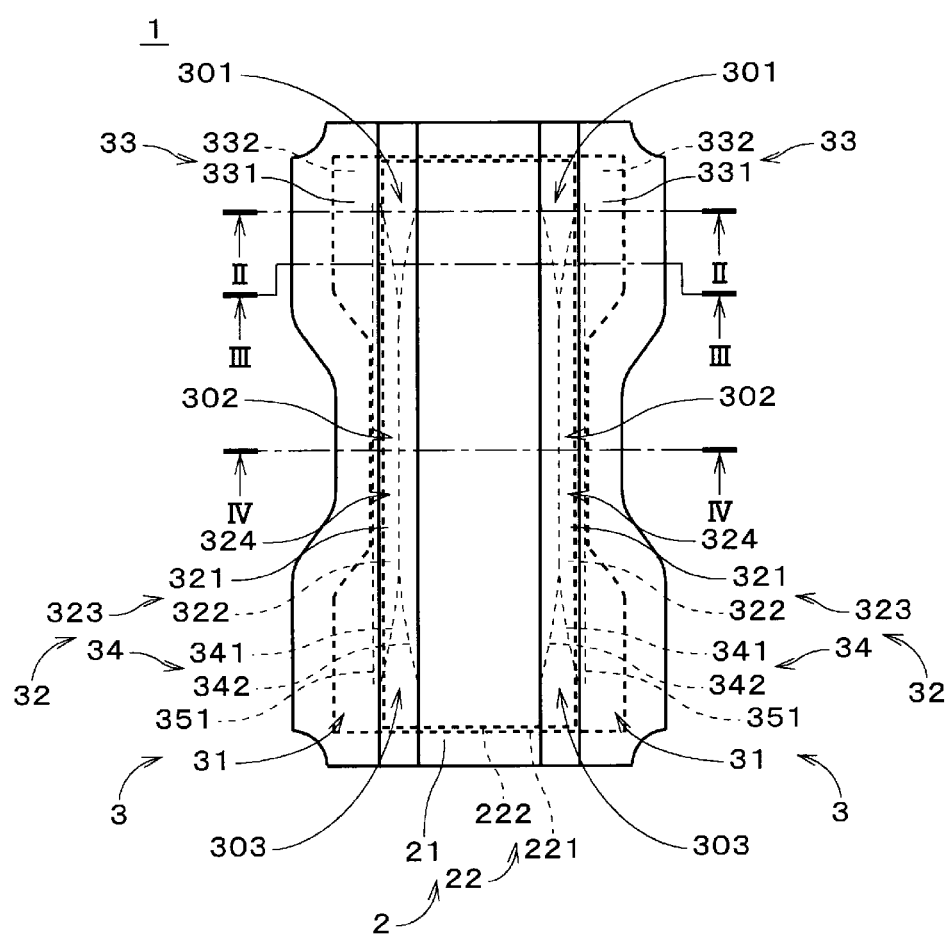
FIG. 1 is a plan view of an auxiliary absorbent pad.

FIG. 1 is a plan view showing an auxiliary absorbent pad 1 when laid out flat according to an embodiment of the present invention. The auxiliary absorbent pad 1 is an absorbent article (or an absorbent product) to be attached to the inner side (i.e., wearer side) of an exterior product such as a disposable diaper that a wearer wears, for receiving body waste (e.g., excrement) from the wearer. In FIG. 1, the auxiliary absorbent pad 1 is illustrated showing, at the near side, the surface of the side that contacts the wearer when the product is worn.

Figure 2:
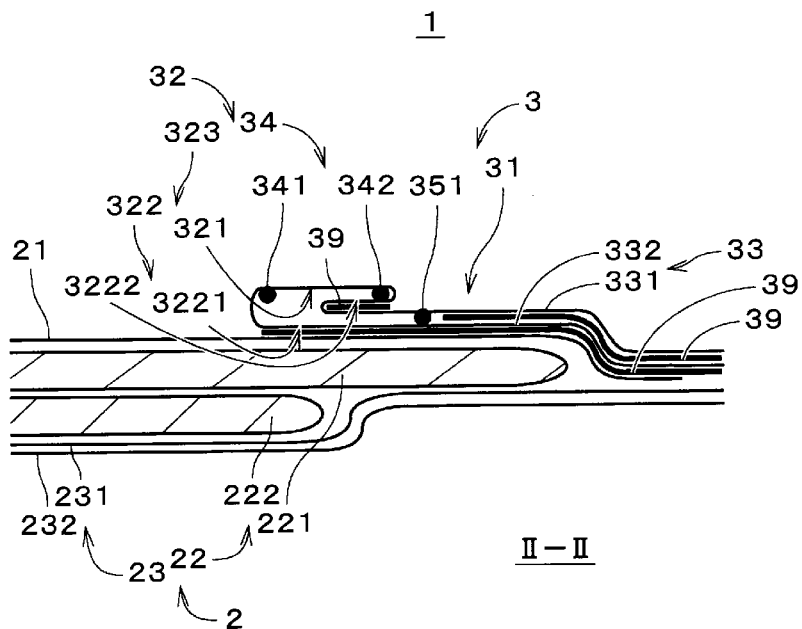
FIG. 2 is a cross-sectional view of the auxiliary absorbent pad.
Figure 3:
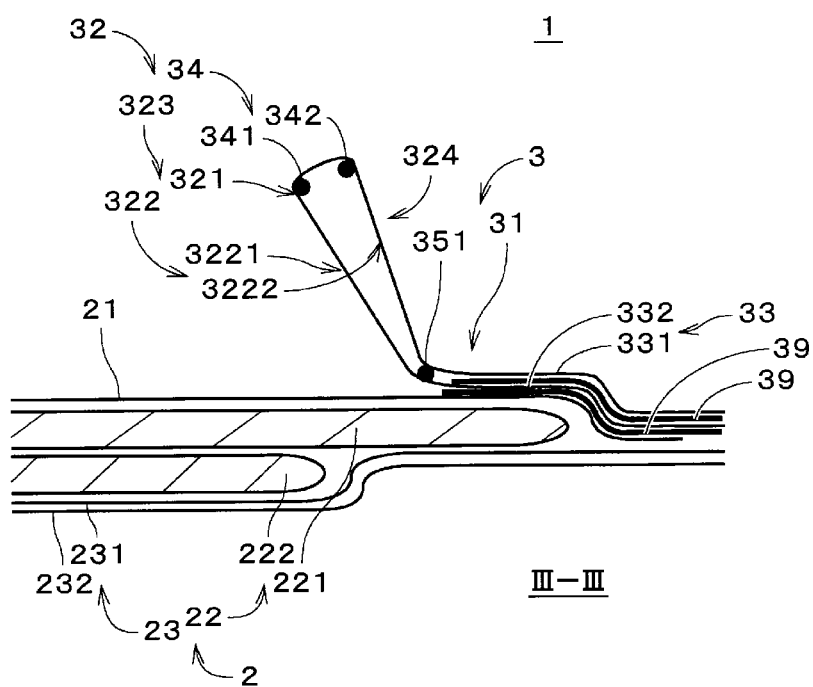
FIG. 3 is a cross-sectional view of the auxiliary absorbent pad.
Figure 4:
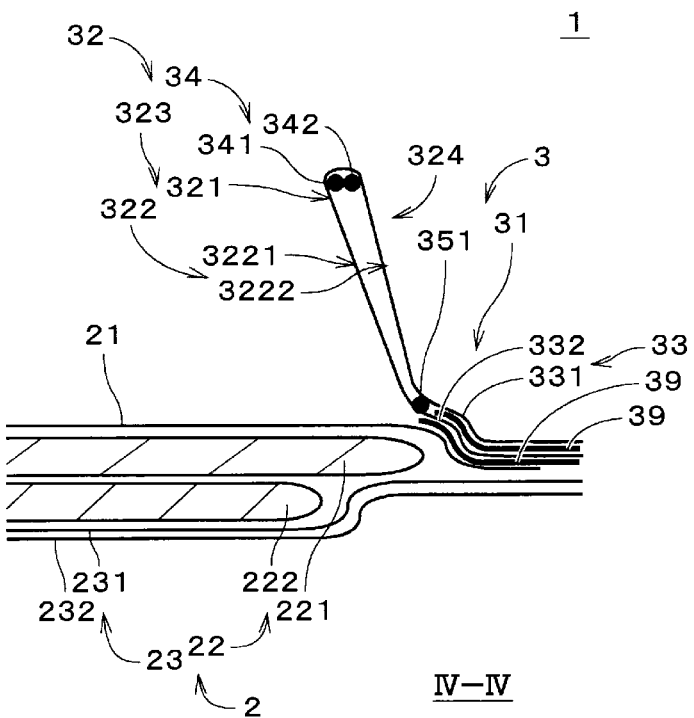
FIG. 4 is a cross-sectional view of the auxiliary absorbent pad.

FIGS. 2 to 4 are cross-sectional views of the auxiliary absorbent pad 1 taken along planes perpendicular to a longitudinal direction (i.e., the vertical direction in FIG. 1) at positions indicated by II-II, III-III, and IV-IV, respectively, in FIG. 1. FIG. 2 shows a cross-section of the auxiliary absorbent pad 1 in the vicinity of one end part in the longitudinal direction, FIG. 4 shows a cross-section of the auxiliary absorbent pad 1 in the vicinity of a central part in the longitudinal direction, and FIG. 3 shows a cross-section of the auxiliary absorbent pad 1 in a boundary part between the end part and the central part. FIGS. 2 to 4 show only right side portions of the sections of the auxiliary absorbent pad 1, and for convenience of illustration, constituent elements of the auxiliary absorbent pad 1 are illustrated apart from each other in a thickness direction (i.e., the vertical direction in FIGS. 2 to 4). Note that the cross-section of the auxiliary absorbent pad 1 in the vicinity of the other end part in the longitudinal direction is the same as in FIG. 2, and the cross-section of the auxiliary absorbent pad 1 in the boundary part between the end part and the central part is the same as in FIG. 3.

As shown in FIGS. 1 to 4, the auxiliary absorbent pad 1 includes a generally sheet-like main body part 2, and two side sheets 3 that are disposed, one on each side of the main body part 2 (i.e., both sides in a width direction that is perpendicular to the longitudinal direction), along substantially the entire length of the main body part 2 in the longitudinal direction.

An upper region and a lower region of the main body part 2 in FIG. 1 are regions that will contact the skin of a wearer on the front side and the back side, respectively, and these regions are respectively referred to as a "front part" and a "rear part" in the following description. Furthermore, a region that is located between and continuous with the front part and the rear part and faces the crotch area of a wearer is referred to as a "central part". In the auxiliary absorbent pad 1, the main body part 2 has the front part, the central part, and the rear part sequentially in the longitudinal direction, and the widths of the front part and the rear part in the width direction are greater than the width of the central part. In other words, the main body part 2 has a so-called hourglass shape in plan view.

As shown in FIGS. 2 to 4, the main body part 2 includes a liquid-pervious top sheet 21, a water-repellent or liquid-impervious back sheet 23, and an absorbent core 22 disposed between the top sheet 21 and the back sheet 23. The back sheet 23 has a layered structure in which a plurality of sheet members (in the present embodiment, two sheet members, namely a first sheet 231 and a second sheet 232) are laminated one above another. The first sheet 231 faces the top sheet 21 and the absorbent core 22, and the second sheet 232 has the same shape as the first sheet 231 and is bonded to the outer surface (i.e., the surface on the opposite side to the wearer, the top sheet 21, and the absorbent core 22) of the first sheet 231.

The absorbent core 22 includes a first absorbing part 221 that faces the top sheet 21 and a second absorbing part 222 that faces the back sheet 23, and the second absorbing part 222 and the first absorbing part 221 are stacked in the thickness direction. The second absorbing part 222 has a generally rectangular shape that is long in the longitudinal direction of the main body part 2, and the first absorbing part 221 extends outwardly in the width direction more than the second absorbing part 222. In order to facilitate comprehension of the diagram, the contours of the first absorbing part 221 and the second absorbing part 222 are indicated by thick broken lines in FIG. 1. As shown in FIG. 1, the width of the first absorbing part 221 in the front part and the rear part is greater than the width of the first absorbing part 221 in the central part. In other words, the first absorbing part 221 has a so-called hourglass shape.

As shown in FIGS. 2 to 4, the top sheet 21 is bonded to the back sheet 23 with a hot-melt adhesive around the absorbent core 22. Furthermore, an outer part 33 of each side sheet 3 in the width direction (which is an outer part of a side-sheet main body 31 described later, and hereinafter referred to as a "base part 33") is bonded with a hot-melt adhesive to a side edge part of the top sheet 21 and a side edge part of the back sheet 23 along the entire lengths of these sheets in the longitudinal direction. In FIGS. 2 to 4, layers 39 of the adhesive adhering to the side sheet 3 are indicated by thick lines. Examples of the above hot-melt adhesive that are used include polyolefin-, rubber-, and vinyl acetate-based adhesives. Note that the bonding of the top sheet 21 and the back sheet 23, the bonding of the side sheets 3, the top sheet 21, and the back sheet 23, and the bonding of parts of the side sheets 3, which will be described later, may be performed through, for example, heat seal bonding or ultrasonic bonding, instead of using an adhesive such as a hot-melt adhesive.

The top sheet 21 is a liquid-pervious sheet material, and quickly catches moisture in the body waste from a wearer and moves the moisture to the absorbent core 22. The top sheet 21 is, for example, a liquid-pervious nonwoven fabric that is formed from hydrophobic fiber (e.g., polypropylene, polyethylene, polyester, polyamide or nylon) whose surface has undergone hydrophilic treatment using a surfactant. Examples of the nonwoven fabric that are used include a point-bond nonwoven fabric, an air-through nonwoven fabric, and a spunbond nonwoven fabric. Note that a nonwoven fabric formed from hydrophilic fiber such as cellulose, rayon, or cotton (e.g., a spunlace nonwoven fabric) may be used as the top sheet 21.

The first absorbing part 221 and second absorbing part 222 of the absorbent core 22 are formed from hydrophilic fiber such as crushed pulp fiber or cellulose fiber. The moisture that has passed through the top sheet 21 is quickly absorbed by the first absorbing part 221 and held in the first absorbing part 221 and the second absorbing part 222. Tissue paper, a liquid-pervious nonwoven fabric or the like that envelops an absorbent material is bonded to the absorbent material with a hot-melt adhesive, thereby preventing the absorbent material from coming off (in particular, coming off after water absorption), for example. Note that the absorbent core 22 may be a single absorbing part that is formed by, for example, blending an absorbent material with hydrophilic fiber.

Examples of the back sheet 23 that are used include a water-repellent or liquid-impervious nonwoven fabric formed from hydrophobic fiber (e.g., a spunbond nonwoven fabric, a meltblown nonwoven fabric, a spunbond-meltblown-spunbond (SMS) nonwoven fabric), a water-repellent or liquid-impervious plastic film, and a layered sheet formed by laminating the above nonwoven fabric and plastic film one above another. Thus, moisture or the like in body waste that reaches the back sheet 23 is prevented from leaking to the outside of the main body part 2. In the present embodiment, a plastic film is used as the first sheet 231 of the back sheet 23, and a nonwoven fabric is used as the second sheet 232. From the viewpoint of preventing the auxiliary absorbent pad 1 from becoming sweaty and improving the comfort of a wearer, it is preferable for the first sheet 231 to be a permeable (breathable) plastic film.

As shown in FIGS. 1 to 4, each side sheet 3 includes a side-sheet main body 31, and a plurality of (three in the present embodiment) string-like elastic elements 341, 342, and 351 that are bonded to the side-sheet main body 31 with a hot-melt adhesive and extend in the longitudinal direction. As described previously, an outer part of the side-sheet main body 31 in the width direction (i.e., a part of the main body part 2 close to a side edge) is a base part 33 that is fixed to the main body part 2. On the other hand, an inner part 32 of the side-sheet main body 31 in the width direction (i.e., a part that is continuous with the base part 33 inwardly of the base part 33, and hereinafter referred to as a "side wall part 32") is not bonded to the top sheet 21 (and other constituent elements), except in both end parts in the longitudinal direction, as shown in FIGS. 2 to 4.

Figure 5A:
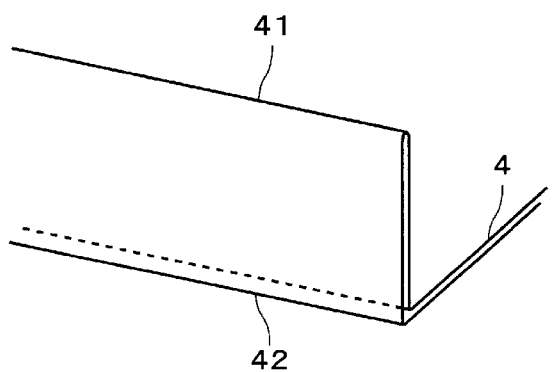
FIG. 5A is a diagram illustrating an example of producing a side-sheet main body.
Figure 5B:
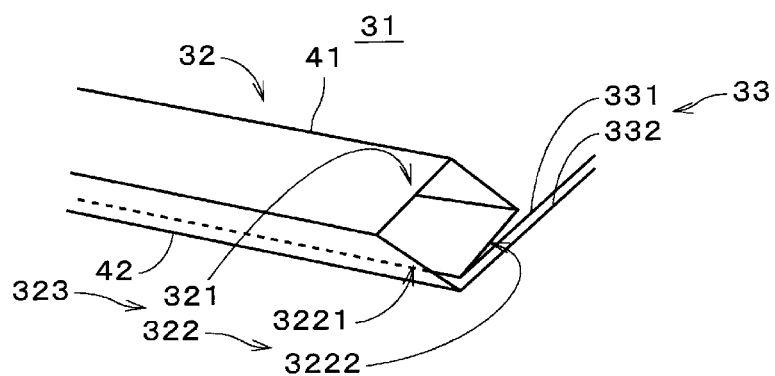
FIG. 5B is a diagram illustrating an example of producing the side-sheet main body.

Here, an example of producing the side-sheet main body 31 will be described in order to facilitate understanding of the structure of the side wall part 32, which is part of the side sheet 3. In this production example, the side-sheet main body 31 is produced such that a sheet 4 that has been folded into two along a predetermined first folding line 41 is vertically folded along a second folding line 42 that is parallel to the first folding line 41 as shown in FIG. 5A, and then, a portion between the first folding line 41 and the second folding line 42 is expanded into a pouch-like shape so that the first folding line 41 roughly overlaps with the second folding line 42 as shown in FIG. 5B. In a part 323 of the side-sheet main body 31 in FIG. 5B that is expanded in a pouch-like shape and that is along the first folding line 41 and the second folding line 42 (hereinafter, referred to as a "strip-like pouch part 323"), a strip-like part 321 located on the upper side in FIG. 5B (hereinafter referred to as a "first strip part 321") and a strip-like part 322 located on the lower side (hereinafter referred to as a "second strip part 322") overlap with each other. In reality, the aforementioned string-like elastic elements 341, 342, and 351 are bonded in advance in their stretched state to the sheet 4. The string-like elastic elements 341 and 342 are positioned on the first strip part 321 inside the strip-like pouch part 323, and the string-like elastic elements 341 and 342 and the strip-like pouch part 323 constitute the side wall part 32.

In the auxiliary absorbent pad 1, the side-sheet main body 31 is bonded to the main body part 2, and in a state in which the main body part 2 is stretched (see FIG. 5B, and FIG. 2 that shows a cross-sectional shape that is substantially unchanged between in the stretched state and in the contracted state), the side wall part 32 includes the first strip part 321 that extends in the longitudinal direction on the main body part 2, and the second strip part 322 that is disposed between the first strip part 321 and the main body part 2 and has both its edges along the longitudinal direction (hereinafter, such edges along the longitudinal direction are simply referred to as "edges") connecting to both edges of the first strip part 321. The second strip part 322 is separated into a strip-like inner part 3221 and a strip-like outer part 3222 in the width direction. The base part 33 of the side-sheet main body 31 includes a first sheet base part 331 that extends outward in the width direction from the inner edge of the outer part 3222, between the outer part 3222 and the main body part 2, and a second sheet base part 332 that is continuous with the inner part 3221 and extends outward in the width direction, between the first sheet base part 331 and the main body part 2.

The two string-like elastic elements 341 and 342 are, as shown in FIG. 1, disposed from the vicinity of one end part 301 of the strip-like pouch part 323 to the vicinity of the other end part 303 in the longitudinal direction, and are bonded to the first strip part 321 with a hot-melt adhesive. In a central part 302 of the strip-like pouch part 323 in the longitudinal direction, the two string-like elastic elements 341 and 342 are positioned on the first folding line 41 in FIG. 5B in close contact with each other in substantially the center of the strip-like pouch part 323 in the width direction, forming a linear shape in the longitudinal direction. Specifically, the two string-like elastic elements 341 and 342 shown in FIG. 1 are close to each other in the width direction while being spaced from both edges of the first strip part 321 in the central part 302 of the strip-like pouch part 323. Furthermore, in the vicinity of the end parts 301 and 303 of the strip-like pouch part 323 in the longitudinal direction, the two string-like elastic elements 341 and 342 are spaced from each other in the width direction, and the vicinity of the tips of the two string-like elastic elements 341 and 342 are positioned on both edges of the first strip part 321.

In the base part 33, a single string-like elastic element 351 (or a plurality of string-like elastic elements) that extends in the longitudinal direction is disposed from the vicinity of one end part of the side wall part 32 to the vicinity of the other end part, and is bonded in its stretched state with a hot-melt adhesive between the first sheet base part 331 and the second sheet base part 332 (see FIG. 2). In the state in which the main body part 2 is stretched, the string-like elastic element 351 is positioned outwardly (outside) of and in the vicinity of the outer edge of the outer part 3222 of the second strip part 322. Note that in the case where the first sheet base part 331 (or the second sheet base part 332) and the first strip part 321 are formed by laminating a plurality of sheets, the string-like elastic elements 341, 342, and 351 may be bonded between these sheets.

In the end parts 301 and 303 of the strip-like pouch part 323 in the longitudinal direction, as shown in FIG. 2, the outer part 3222 of the second strip part 322 is bonded to the first sheet base part 331 with a hot-melt adhesive, and the inner part 3221 is bonded to the (top sheet 21 of the) main body part 2. Furthermore, the second sheet base part 332 is bonded to the top sheet 21 and the back sheet 23 in substantially its entirety from the vicinity of the inner part 3221 to the outer edge in the width direction. Specifically, substantially the entire surface of the second sheet base part 332 that faces the main body part 2 is bonded to the main body part 2.

On the other hand, in the part other than the two end parts 301 and 303, the outer part 3222 and inner part 3221 of the second strip part 322 are not bonded to any of the members (see FIGS. 3 and 4). Furthermore, the second sheet base part 332 is bonded to the top sheet 21 and the back sheet 23 only outwardly (outside) of the string-like elastic element 351 in the width direction. Note that in the side wall part 32 as a whole, the first sheet base part 331 is bonded to the second sheet base part 332 outwardly of the string-like elastic element 351 in the width direction, and the first strip part 321 and the second strip part 322 are not bonded to each other.

One example of the side-sheet main body 31 that is used is a water-repellent or liquid-impervious nonwoven fabric formed from hydrophobic fiber (e.g., a spunbond nonwoven fabric, a meltblown nonwoven fabric, or an SMS nonwoven fabric). Examples of the string-like elastic elements 341, 342, and 351 that are used include polyurethane yarn and string-like natural rubber, and in the present embodiment, polyurethane yarn is used as each string-like elastic element. Note that the side-sheet main body 31 does not necessarily have to be formed from a single sheet 4, and the side-sheet main body 31 having the above-described structure may be formed by partially bonding a plurality of sheets.

In the auxiliary absorbent pad 1, a standing part 324 of the strip-like pouch part 323 that stands up from the main body part 2 is formed by contraction of a set of the string-like elastic elements 341 and 342 that are a side wall part-elastic member 34. Accordingly, in a state in which a wearer wears an exterior product that has the auxiliary absorbent pad 1 attached therein, the two side wall parts 32 extending in the longitudinal direction stand up from the main body part 2 toward the wearer, one on each side of the main body part 2, forming a pair of standing gathers that comes into contact with the vicinity of the top of the wearer's legs.

In this case, in the central part 302 of the strip-like pouch part 323, as shown in FIG. 4, each strip-like pouch part 323 stands up with the inner part 3221 and outer part 3222 of the second strip part 322 facing each other. Furthermore, since the string-like elastic elements 341 and 342 are positioned on the first folding line 41 (see FIG. 5B), the strip-like pouch part 323 is in a folded state along the first folding line 41, and the upper end of the standing part 324 is in linear contact with the groin area of the wearer. Furthermore, gathers are formed in the vicinity of the string-like elastic element 351 in the base part 33 by contraction of the string-like elastic element 351, which serves as a base-part elastic member. Because a portion of the base part 33 inwardly (inside) of the string-like elastic element 351 (the left side in FIG. 4) is not bonded to the main body part 2, this portion also stands up from the main body part 2, and the lower portion (i.e., the second strip part 322) of the strip-like pouch part 323 is spaced from the main body part 2.

In the end parts 301 and 303 of the strip-like pouch part 323 in the longitudinal direction, as shown in FIG. 2, substantially the entire second strip part 322 is directly or indirectly bonded to the main body part 2, and as a result, a state in which the first strip part 321 and the second strip part 322 overlap with each other (i.e., they are in contact with each other) and a state in which the second strip part 322 overlaps with the main body part 2 are maintained. In this way, the strip-like pouch parts 323 do not stand up and there are no standing parts 324 in the end parts 301 and 303.

In the boundary part between each of the end parts 301 and 303 and the central part 302 (which is a part where the shape of the strip-like pouch part 323 transitions, and thus can also be taken as a transition part, as will be described later), as shown in FIG. 3, the string-like elastic elements 341 and 342 are spaced from each other in the width direction, and the upper end (i.e., a part between the string-like elastic elements 341 and 342) of the standing part 324 contacts the skin of a wearer in roughly planar form. Furthermore, since the second sheet base part 332 and the main body part 2 are not bonded to each other inwardly of the string-like elastic element 351 (the left side in FIG. 3), the lower part of the strip-like pouch part 323 is spaced from the main body part 2, as with the central part 302 of the strip-like pouch part 323. In reality, in the boundary part, the width of the upper end of the standing part 324 gradually increases and the distance between the upper end of the standing part 324 and the main body part 2 (i.e., the height of the upper end of the standing part 324 from the main body part 2) gradually decreases at positions approaching the end parts 301 and 303 from the central part 302.

As described above, the auxiliary absorbent pad 1 is provided with the first strip part 321 extending in the longitudinal direction and the second strip part 322 disposed between the first strip part 321 and the main body part 2 and having both its edges connecting to both edges of the first strip part 321, in the state in which the main body part 2 is stretched, and the strip-like pouch part 323 is formed from the first strip part 321 and the second strip part 322. Furthermore, in the central part 302 of the strip-like pouch part 323, the side wall part-elastic member 34 extending in the longitudinal direction is bonded to the first strip part 321 away from both edges of the first strip part 321. In the end parts 301 and 303 of the strip-like pouch part 323, a state in which the first strip part 321 overlaps with the second strip part 322, and the second strip part 322 overlaps with the main body part 2 (i.e., a state in which the strip-like pouch part 323 is folded and overlaps with the main body part 2) is maintained. This allows the height of the upper end of the standing part 324, which contacts the wearer, from the main body part 2 to be gradually changed in the longitudinal direction in the boundary part between each of the end parts 301 and 303 and the central part 302 of the strip-like pouch part 323. As a result, in the auxiliary absorbent pad 1 in which the standing parts 324 stand up high in the central part 302, it is possible to allow the (upper ends of the) standing parts 324 to fit against the skin of the wearer from the central part 302 toward the end parts 301 and 303, and to thereby prevent leakage of body waste from between the wearer and the standing parts 324. It is also possible to reduce the degree of pressure applied by the standing parts 324 to the skin of the wearer in the boundary part.

Furthermore, in the auxiliary absorbent pad 1, positioning the side wall part-elastic member 34 in substantially the center of the strip-like pouch part 323 in the width direction in the central part 302 of the strip-like pouch part 323 allows the standing parts 324 to stand up high in the central part 302. In addition, bonding the second sheet base part 332 to the main body part 2 outwardly of the strip-like pouch part 323 in the vicinity of the central part 302 further allows the standing parts 324 to stand up high in the central part 302.

While the above has been a description of an embodiment of the present invention, the present invention is not intended to be limited to the above-described embodiment and can be modified in various ways.

If the side wall part-elastic member 34 is bonded to the first strip part 321 away from the edges of the first strip part 321 (i.e., in the central part 302, there is no elastic member in the vicinity of the edges of the first strip part 321, and the elastic member is not bonded to the second strip part 322), it may be disposed at a position that is shifted from the center of the strip-like pouch part 323 in the width direction. In this case as well, the side wall part 32 can be caused to stand up to a certain degree in the central part 302.

Figure 6:
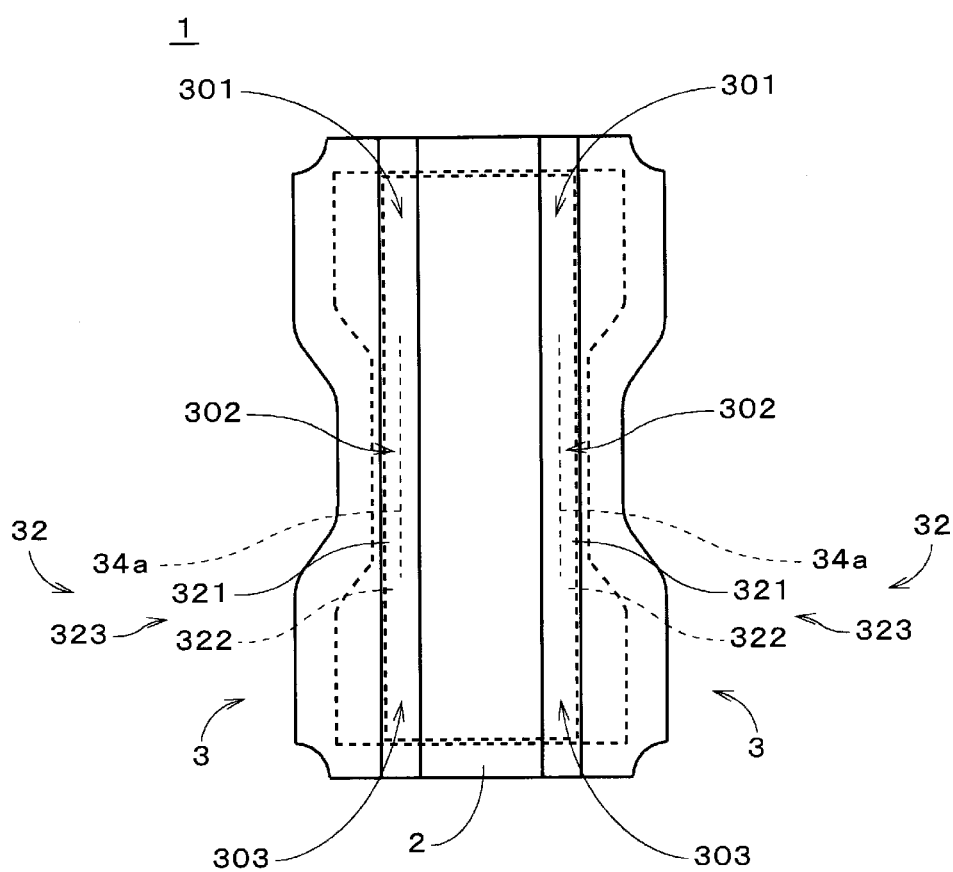
FIG. 6 is a diagram showing another example of the auxiliary absorbent pad.

Furthermore, although in the auxiliary absorbent pad 1 of FIG. 1, the side wall part-elastic member 34 is disposed from the vicinity of one end part 301 of the strip-like pouch part 323 to the vicinity of the other end part 303, for example, a side wall part-elastic member 34a may be provided in only the vicinity of the central part 302 of each strip-like pouch part 323 as shown in FIG. 6. In this case, in the central part 302 of the strip-like pouch part 323, the upper end of the standing part 324 is in linear contact with the skin of the wearer as in FIG. 4, and in the end parts 301 and 303 of the strip-like pouch part 323, a state in which the strip-like pouch part 323 is folded and overlaps with the main body part 2 is maintained as in FIG. 2. Furthermore, in the boundary parts between the central part 302 and the end parts 301 and 303, due to the effect of contraction of the side wall part-elastic member 34a in the central part 302, the width of the upper end of the standing part 324 gradually increases and the height of the upper end of the standing part 324 from the main body part 2 gradually decreases at positions approaching the end parts 301 and 303 from the central part 302. This allows each standing part 324 to fit against the skin of the wearer in the boundary parts and also reduces the degree of pressure applied by the standing part 324 to the skin of the wearer.

Meanwhile, in order to bring each standing part 324 in close contact with the wearer in the boundary parts as well, it is preferable for the side wall part-elastic member to be disposed from the vicinity of one end part 301 of the strip-like pouch part 323 to the vicinity of the other end part 303 in the longitudinal direction. In this case, in order to appropriately form the standing part 324 such that the height of the upper end of the standing part 324 from the main body part 2 gradually changes in the boundary parts, it is preferable that, as in the auxiliary absorbent pad 1 of FIG. 1, the (sum of the) distances between the side wall part-elastic member 34 and the edges of the first strip part 321 in the vicinity of each of the end parts 301 and 303 are shorter than the (sum of the) corresponding distances in the central part 302.

Figure 7:
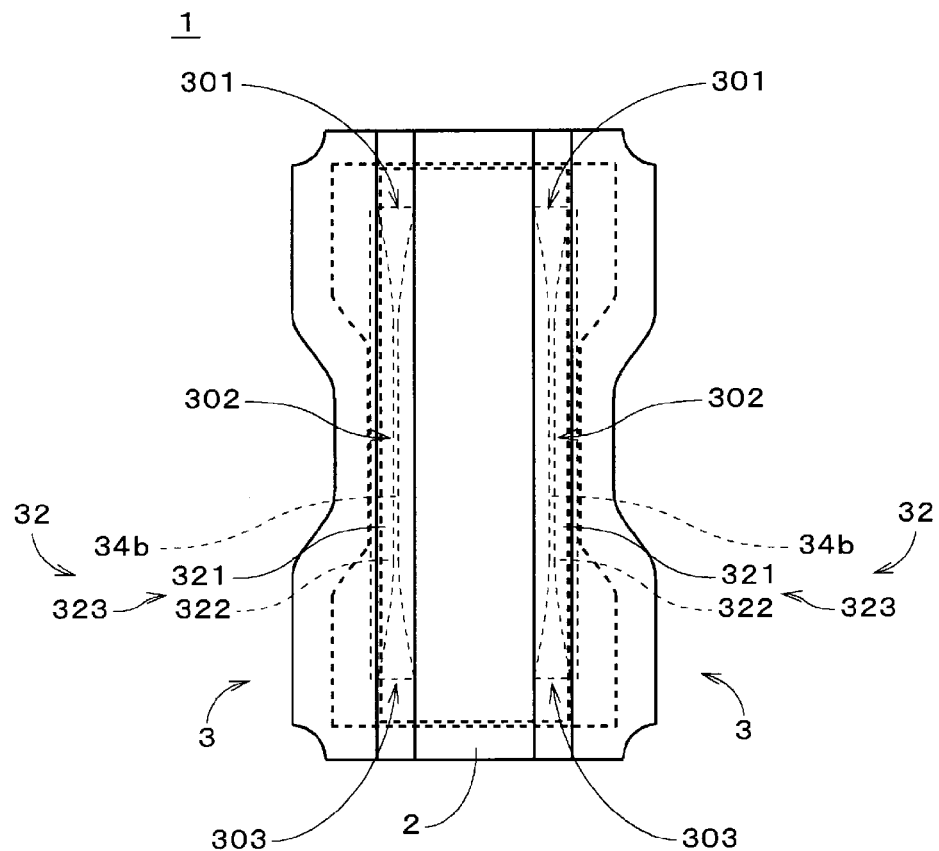
FIG. 7 is a diagram showing yet another example of the auxiliary absorbent pad.

The side wall part-elastic member having the above-described structure can also be realized by, for example, a strip-like side wall part-elastic member 34b formed from a strip-like polyurethane film, natural rubber, or the like as shown in FIG. 7. Each side wall part-elastic member 34b in FIG. 7 has a wider width in the vicinity of the end parts 301 and 303 than that in the central part 302.

Note that the side wall part-elastic member may be realized by three or more string-like elastic elements, for example with a method such as disposing one or more other string-like elastic elements between the two string-like elastic elements 341 and 342 disposed in an X shape.

Figure 8:
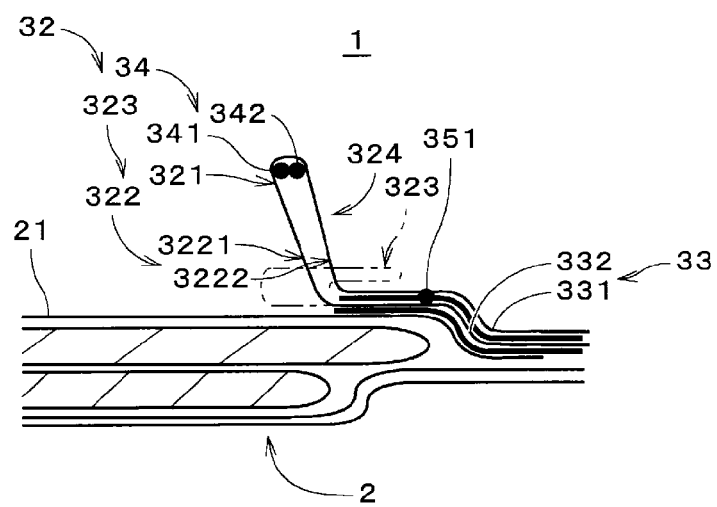
FIG. 8 is a diagram showing yet another example of the auxiliary absorbent pad.

Depending on the design of the auxiliary absorbent pad 1, the entire second sheet base part 332 may also be bonded to the main body part 2 in the central part 302 as shown in FIG. 8. In FIG. 8, a strip-like pouch part 323 in the state in which the main body part 2 is stretched is illustrated by the chain double-dashed line. In the auxiliary absorbent pad 1 of FIG. 8, the standing part 324 is formed by using the adjacent edges of the inner part 3221 and the outer part 3222 as fixed edges.

In the central part 302 of the strip-like pouch part 323, in the state in which the standing part 324 stands up, portions of the first strip part 321 that face each other may be bonded in their entirety or in parts, and portions of the second strip part 322 may be bonded in their entirety or in parts (i.e., sheets that face each other from the second folding line 42 to the upper edge in FIG. 5A).

The strip-like pouch part may be realized in various forms, and the inner part 3221 and outer part 3222 of the second strip part 322 do not necessarily have to be separated from each other (i.e., the inner part 3221 and the outer part 3222 may be continuous).

Although in the above-described embodiment, substantially the entire second strip part 322 is bonded to the main body part 2 in the end parts 301 and 303 of the strip-like pouch part 323 in the longitudinal direction (see FIG. 2), a configuration is, for example, also possible in which, if the state in which the first strip part 321 and the second strip part 322 overlap with each other and the state in which the second strip part 322 overlaps with the main body part 2 are maintained, only the vicinities of the edges of the second strip part 322 are bonded to the main body part 2, or the first strip part 321 and the second strip part 322 are bonded in parts to each other and the second strip part 322 and the main body part 2 are bonded in parts to each other.

In the auxiliary absorbent pad 1, the back sheet 23 may be a single-layer sheet member, or a laminate assembly of three or more sheet members.

The configuration of the auxiliary absorbent pad 1 according to the above-described embodiment may be applied to, for example, a tape-type disposable diaper that is made to be worn by fixing together a portion that comes into contact with the front side of the wearer and a portion that comes into contact with the back side around the waistline, or a pants-type disposable diaper that has a waist opening at the top end and a pair of leg openings at the bottom end. In this way, the configuration of the auxiliary absorbent pad 1 may be applied to other absorbent articles such as disposable diapers.

The configurations of the above-described embodiment and variations may be appropriately combined as long as there are no mutual inconsistencies.

While the invention has been shown and described in detail, the foregoing description is in all aspects illustrative and not restrictive. It is therefore understood that numerous modifications and variations can be devised without departing from the scope of the invention.

REFERENCE SIGNS LIST

1 Auxiliary absorbent pad
2 Main body part
3 Side sheet
21 Top sheet
22 Absorbent core
23 Back sheet
32 Side wall part
34, 34a, 34b Side wall part-elastic member 301, 303 End part
302 Central part
321 First strip part
322 Second strip part
323 Strip-like pouch part
324 Standing part
331 First sheet base part
332 Second sheet base part
341, 342 String-like elastic element
3221 Inner part
3222 Outer part

The invention claimed is:

1. An absorbent article for receiving body waste from a wearer, comprising:
    a generally sheet-like main body part having an absorbent core disposed between a back sheet and a top sheet; and
    two side wall parts that extend in a longitudinal direction of said main body part, one on each side of said main body part,
    wherein each side wall part includes:
    a strip-like pouch part that includes a first strip part and a second strip part, said first strip part extending in said longitudinal direction on said main body part and said second strip part being disposed between said first strip part and said main body part and having both edges along said longitudinal direction, in a state in which said main body part is stretched, said both edges of said second strip part connecting to both edges of said first strip part, respectively; and
    an elastic member that is bonded to said first strip part and disposed from a vicinity of one end part of said strip-like pouch part to a vicinity of the other end part in said longitudinal direction,
    in a central part of said strip-like pouch part in said longitudinal direction, said elastic member extends linearly in said longitudinal direction and said elastic member is located in approximately a center of said strip-like pouch part in a width direction that is perpendicular to said longitudinal direction and away from said both edges of said first strip part,
    distances between said elastic member and said both edges of said first strip part in the vicinity of both end parts of said strip-like pouch part in said longitudinal direction are shorter than said distances in said central part
    a standing part that stands up from said main body part is formed in said strip-like pouch part by contraction of said elastic member, and
    in said both end parts, a state in which said first strip part and said second strip part overlap with each other and a state in which said second strip part overlaps with said main body part are maintained.

2. The absorbent article according to claim 1, wherein said elastic member is a group of two string-like elastic elements that are disposed from the vicinity of said one end part to the vicinity of said other end part, and
    said two string-like elastic elements are close to each other in said width direction in said central part and are spaced from each other in said width direction in the vicinity of said both end parts.

3. The absorbent article according to claim 2, wherein two side sheets are disposed, one on said each side of said main body part,
    said each side wall part is a portion of one of said side sheets,
    in said each side wall part that is in the state in which said main body part is stretched, said second strip part is separated into a strip-like inner part and a strip-like outer part in said width direction,
    each of said side sheets includes:
    a first sheet base part that extends outward in said width direction from an inner edge of said outer part, between said outer part and said main body part; and
    a second sheet base part that is continuous with said inner part and extends outward in said width direction, between said first sheet base part and said main body part, and
    in said both end parts, a surface of said second sheet base part that faces said main body part is bonded to said main body part, and in a vicinity of said central part, said second sheet base part is bonded to said main body part outwardly of said strip-like pouch part.

4. The absorbent article according to claim 1, wherein two side sheets are disposed, one on said each side of said main body part,
    said each side wall part is a portion of one of said side sheets,
    in said each side wall part that is in the state in which said main body part is stretched, said second strip part is separated into a strip-like inner part and a strip-like outer part in said width direction,
    each of said side sheets includes:
    a first sheet base part that extends outward in said width direction from an inner edge of said outer part, between said outer part and said main body part; and
    a second sheet base part that is continuous with said inner part and extends outward in said width direction, between said first sheet base part and said main body part, and
    in said both end parts, a surface of said second sheet base part that faces said main body part is bonded to said main body part, and in a vicinity of said central part, said second sheet base part is bonded to said main body part outwardly of said strip-like pouch part.

* * * * *